(12) United States Patent
Chang et al.

(10) Patent No.: US 10,376,488 B2
(45) Date of Patent: Aug. 13, 2019

(54) USE OF FLAVONOIDS IN MANUFACTURING COMPOSITIONS FOR WOUND HEALING

(71) Applicant: ONENESS BIOTECH CO., Ltd, Taipei (TW)

(72) Inventors: Wei-Luen Chang, Taipei (TW); Mo-Chi Cheng, Taipei (TW)

(73) Assignee: ONENESS BIOTECH CO., LTD, Taipei (TW)

( * ) Notice: Subject to any disclaimer, the term of this patent is extended or adjusted under 35 U.S.C. 154(b) by 0 days.

(21) Appl. No.: 15/509,121

(22) PCT Filed: Sep. 5, 2014

(86) PCT No.: PCT/CN2014/086034
§ 371 (c)(1),
(2) Date: Mar. 6, 2017

(87) PCT Pub. No.: WO2016/033802
PCT Pub. Date: Mar. 10, 2016

(65) Prior Publication Data
US 2017/0273938 A1    Sep. 28, 2017

(51) Int. Cl.
*A61K 31/352*    (2006.01)

(52) U.S. Cl.
CPC .................................. *A61K 31/352* (2013.01)

(58) Field of Classification Search
None
See application file for complete search history.

(56) References Cited

PUBLICATIONS

Bower, A. et al. J. Agricult. Food Chem. 2014 vol. 62, pp. 6147-6158.*
Nyiligira, E. et al J. Ethnophamarcol 2008 vol. 119, pp. 680-685.*
Majtan, J. et al., Arch Dermatol Res 2013 vol. 305 pp. 619-627.*
Ganie, S. et al., BioMed Res Intl 2014 Article No. 401213.*

* cited by examiner

*Primary Examiner* — Heidi Reese
(74) *Attorney, Agent, or Firm* — Birch, Stewart, Kolasch & Birch, LLP

(57) ABSTRACT

Disclosed is a method for wound healing comprising administering a subject in need thereof a therapeutically effective amount of a flavonoid compound, wherein the compound is preferably nonglycosylated flavone. Specifically, the present invention can be used for treating skin symptoms of a trauma, a burn, a scald and a chronic wound, and can be particularly used for healing a wound of a diabetes patient.

4 Claims, No Drawings

USE OF FLAVONOIDS IN MANUFACTURING COMPOSITIONS FOR WOUND HEALING

CROSS REFERENCE TO RELATED APPLICATIONS

The present application is a 371 national phase application of PCT Application No. PCT/CN2014/086034, filed Sep. 5, 2014.

FIELD OF THE INVENTION

The present invention discloses a new use of a compound in the preparation of a wound healing composition. Particularly, the present invention involves a new use of a flavonoid compound in the preparation of a wound healing composition.

BACKGROUND OF THE INVENTION

Flavonoids are refer generally to a series of compounds having two benzene rings containing phenolic hydroxyl groups, mutually connected with the central three-carbon atoms, having the structure shown as the general formula:

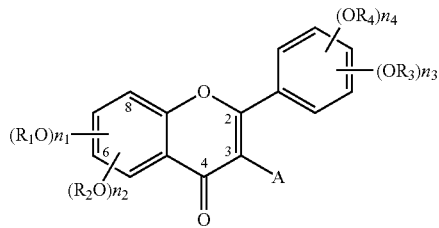

They are generally found in fruits, vegetables, tea, grape wine, seeds, or plant roots etc. Although they are not belonged as vitamins, they are demonstrated to have anti-oxidation functions and anti-inflammatory reaction effects, and also confirmed to have the effects of resisting or relieving the formation of tumors, relieving pain and relieving cardiovascular diseases or malaemia.

Flavonoids include flavones and flavonols. Flavones also include glycosylated flavones and non-glycosylated flavones.

U.S. Pat. No. 7,471,973 B2 issued on Oct. 29, 2002 disclose that flavonoids can be used in cosmetics but does not mention other effects. In addition, U.S. Pat. No. 6,451,837B1 issued on Sep. 17, 2002 discloses the neuroprotective effects of flavonoids.

SUMMARY OF THE INVENTION

The purpose of the present invention is to provide a new use of flavonoids in the preparation of a wound healing composition.

In one aspect, the present invention provides a method for wound healing comprising administering to a patient in need thereof a therapeutically effective amount of a compound of the structure as shown in the general formula I or an isomer thereof:

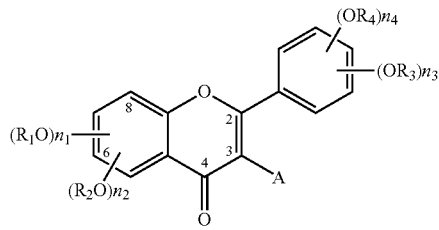

Formula I wherein A is a hydrogen atom, R or —OH;
$n_1$ and $n_2$ are the same or different, being an integer of 0 to 4, wherein the sum of $n_1$ and $n_2$ is equal to or less than 4;
$n_3$ and $n_4$ are the same or different, being an integer of 0 to 5, wherein the sum of $n_3$ and $n_4$ is at most equal to 5;
wherein R, $R_1$, $R_2$, $R_3$ or $R_4$ is a hydrogen atom, an alkyl group having 1 to 30 carbon atoms, an acyl group having an alkyl group having 1 to 30 carbon atoms, or a hydrocarbon chain having 1 to 30 carbon atoms;
or a pharmaceutically acceptable ester or salt thereof.

According to the present invention, the method is used for treating and/or healing wounds, including skin symptoms of trauma, burns and scalds and chronic wounds, and particularly diabetic wounds.

According to one example of the present invention, the compound is a flavone, particularly a non-glycosylated flavone.

According to the preferred embodiment of the present invention, the non-glycosylated flavone compound is cirsimaritin, and has the following structure:

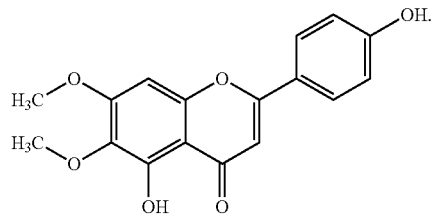

Those and other aspects of the present invention may be further clarified by the following descriptions and drawings of preferred embodiments. Although there may be changes or modifications therein, they would not betray the spirit and scope of the novel ideas disclosed in the present invention.

DETAILED DESCRIPTION OF THE INVENTION

Unless defined otherwise, all technical and scientific terms used herein have the same meanings as commonly understood by one of skill in the art to which this invention belongs.

Unless clearly specified herein, meanings of the articles "a," "an," and "said" all include the plural form of "more than one." Therefore, for example, when the term "a component" is used, it includes multiple said components and equivalents known to those of common knowledge in said field.

The present invention provides a method for wound healing comprising administering to a patient in need thereof a therapeutically effective amount of a compound of the structure as shown in the general formula I or an isomer thereof:

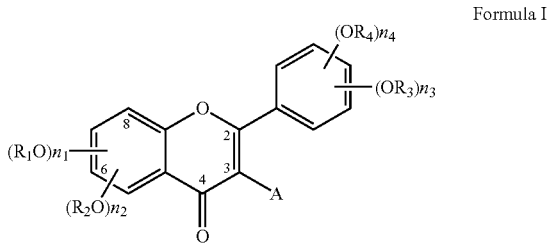

Formula I wherein A is a hydrogen atom, R or —OH;
$n_1$ and $n_2$ are the same or different, being an integer of 0 to 4, wherein the sum of $n_1$ and $n_2$ is equal to or less than 4;
$n_3$ and $n_4$ are the same or different, being an integer of 0 to 5, wherein the sum of $n_3$ and $n_4$ is at most equal to 5;
wherein R, $R_1$, $R_2$, $R_3$ or $R_4$ is a hydrogen atom, an alkyl group having 1 to 30 carbon atoms, an acyl group having an alkyl group having 1 to 30 carbon atoms, or a hydrocarbon chain having 1 to 30 carbon atoms;
or a pharmaceutically acceptable ester or salt thereof.

According to the present invention, the compound is a flavone, particularly a non-glycosylated flavone. The non-glycosylated flavone is cirsimaritin, and has the following structure:

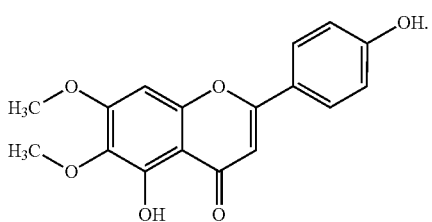 [SMILES: COc1cc2oc(-c3ccc(O)cc3)cc(=O)c2c(O)c1OC]

According to the invention, the composition of the present invention comprises a pharmaceutically acceptable carrier.

According to the invention, the pharmaceutically acceptable carrier comprises an appropriate excipient and is prepared as an external medicament form, a cosmetic form or pharmaceutical form.

According to the invention, the composition further comprises a therapeutic agent, for example, other anti-inflammatory agents, antibacterial agents or other therapeutic agents.

As used herein, the term "skin symptoms" includes wounds or sores, including skin injuries such as incised injuries, lacerated injuries, stabbing injuries, wear injuries, etc. in skin. According to the present invention, the compounds show the effects in healing wounds for skin symptoms of trauma, burns and scalds and chronic wounds. In particular, the method of the invention in effective in treating diabetic wounds, for example, chronic wounds of diabetic present patients.

As used herein, the term "treatment" includes the meaning of "treating" or "promoting" which means improving symptoms.

As used herein, the term "patient" encompasses humans, and animals, particularly mammals.

As used herein, the term "pharmaceutically acceptable carrier" refers to a diluent, excipient or the like as used in a commonly used technique for the preparation of a pharmaceutical composition. According to the present invention, a medicament form, a cosmetic form, or a pharmaceutical material form can be made. According to the present invention, a form for local application can be made for example, in the form of a spray. Spray forms include a spray agent and a liquid agent; or in a semi-solid form or a solid form, preferably a solid form with dynamic viscosity greater than that of water. Appropriate formulations include, but are not limited to, suspension, emulsion, cream, ointment, liniment, etc. Preferably, it is in the form of an ointment. The pharmaceutical composition of the present invention, no matter what form it is, can further include emollient, fragrances or pigments to improve their acceptability for various uses.

As used herein, the term "therapeutically effective amount" refers to a dosage that can effectively treat injuries for treatment of symptoms. The appropriate dosage can be used based on the needs of patients or wounds and according to technologies and clinical knowledge commonly used in pharmaceutics, and adjusted according to the manners and treatment conditions of the application, including age, body weight, symptoms, treatment effects, application modes and treatment time.

The present invention is illustrated in the above description of the invention and the following examples, which are not intended for limiting the scope of the present invention.

EXAMPLE 1

Establishment of Animal Testing Mode

After rats' body weight reach 300 g, the induction of hyperglycemia was carried out with streptozotocin (STZ) (65 mg/kg, ip administration). Choosing animals with successfully induced hyperglycemia (300 mg/DL), the hyperglycemic animals were subjected to diabetic wound healing tests two months after the onset of hyperglycemic symptoms. Hyperglycemic animals with a body weight less than 300 g were excluded, and random grouping was performed. Animals were anesthetized with pentobarbital and then their backs were shaved and disinfected. Three pieces of animal skin (full thickness) were harvested from the back of the animals at points 4, 6 and 8 cm from the midpoint of the two scapula with an 1- cm-diameter drilling round knife.

Wounds of each animal were applied with testing agents. New skins were harvested for examination after the end of experiment.

Analyzing the areas of the three wounds on the back of each rat by image pro with the area on day zero as the original wound area. The original wound area is subtracted by the wound area at each time point and then divided by the original wound area to serve as the percentage of wound healing. The average value of the three percentages of wound healing of each rat is considered as the respective would healing extent of each rat. The number of rats was 6 for each group of each test. Data is expressed as mean±SEM. P value is calculated for the test results by t-test against control group, where P<0.05 indicates significant differences, denoted *.

A 0.5% cirsimaritin composition was prepared in an ointment form, and was applied to the rats as treated above. The results are as follows. The comparison between the percentages of wound healing at 9, 11, 13, and 15 days after administration, and the untreated control group is shown below. There were significant differences for each group. The wound half-closure time (CT50 value) was further calculated and also shows significant differences.

| | Days after administration (%) | | | | |
|---|---|---|---|---|---|
| | 9 | 11 | 13 | 15 | CT50 |
| Control group | 20.4 ± 4.1 | 35.0 ± 2.8 | 56.1 ± 2.8 | 67.7 ± 3.1 | 13.3 ± 0.4 |
| cirsimaritin (0.5%) | 37.2 ± 3.9* | 51.5 ± 3.1* | 70.6 ± 3.5* | 83.3 ± 3.2* | 10.7 ± 0.4* |

%: percentage of wound healing
CT50: wound half-closure time
*$p < 0.05$
Number of animals: n = 6

It is can be concluded from the results that the compounds of the present invention (taking cirsimaritin as an example) have the effects in healing of chronic wounds of diabetic patients.

We claim:

1. A method for healing a chronic wound comprising topically administering to a patient in need thereof a therapeutically effective amount of a compound of the structure as shown in the general formula I:

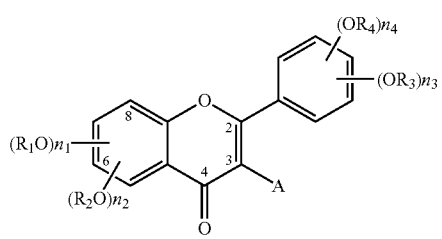

Formula I wherein A is a hydrogen atom, R or —OH;
$n_1$ and $n_2$ are the same or different, being an integer of 0 to 4, wherein the sum of $n_1$ and $n_2$ is equal to or less than 4;
$n_3$ and $n_4$ are the same or different, being an integer of 0 to 5, wherein the sum of $n_3$ and $n_4$ is equal to or less than 5;
wherein R, $R_1$, $R_2$, $R_3$ or $R_4$ is a hydrogen atom, or an alkyl group having 1 to 3 carbon atoms, and
wherein the compound is a non-glycosylated flavone.

2. The method of claim 1, wherein the compound is cirsimaritin and has the following structure:

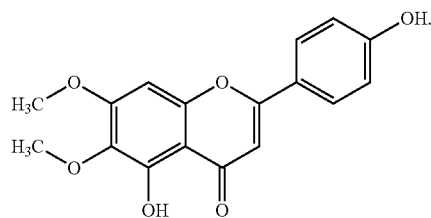 [SMILES: COc1cc2oc(-c3ccc(O)cc3)cc(=O)c2c(O)c1OC]

3. The method of claim 1, wherein the compound is associated with a pharmaceutically acceptable carrier and is prepared as a composition in an external medicament form, a cosmetic form, or a pharmaceutical form.

4. The method of claim 2, wherein the compound is associated with a pharmaceutically acceptable carrier and is prepared as a composition in an external medicament form, a cosmetic form, or a pharmaceutical form.

* * * * *